United States Patent [19]
Gaster

[11] Patent Number: 5,817,833
[45] Date of Patent: Oct. 6, 1998

[54] BIPHENYLAMIDE COMPOUNDS AS $5HT_{1D}$ ANTAGONISTS

[75] Inventor: Laramie Mary Gaster, Bishop's Stortford, United Kingdom

[73] Assignee: SmithKline Beecham p.l.c., Brentford, England

[21] Appl. No.: 793,428

[22] PCT Filed: Aug. 14, 1995

[86] PCT No.: PCT/EP95/03226

§ 371 Date: Feb. 21, 1997

§ 102(e) Date: Feb. 21, 1997

[87] PCT Pub. No.: WO96/06079

PCT Pub. Date: Feb. 29, 1996

[30] Foreign Application Priority Data

Aug. 23, 1994 [GB] United Kingdom ............ 9416972

[51] Int. Cl.[6] .................. C07D 209/36; C07D 209/26; A61K 31/40
[52] U.S. Cl. .................. 548/484; 548/500; 514/421
[58] Field of Search .................. 548/484, 500; 514/421

[56] References Cited

U.S. PATENT DOCUMENTS

| | | | |
|---|---|---|---|
| 3,470,203 | 9/1969 | Gal | 540/484 X |
| 3,860,609 | 1/1975 | Lundt | 548/484 |
| 4,059,583 | 11/1977 | McComsey et al. | 548/484 X |
| 5,578,633 | 11/1996 | Wagnon et al. | 514/418 |

FOREIGN PATENT DOCUMENTS

| | | |
|---|---|---|
| 0750943 | 11/1970 | Belgium ................ 548/484 |
| 0 533 266 A1 | 3/1993 | European Pat. Off. . |
| 0 533 267 A1 | 3/1993 | European Pat. Off. . |
| WO 95/06637 | 3/1995 | WIPO . |

OTHER PUBLICATIONS

Clitherow, et al., Journal Of Medicinal Chemistry, vol. 37, No. 15, 1994; pp. 2253–2257.

*Primary Examiner*—Floyd D. Higel
*Attorney, Agent, or Firm*—Wayne J. Dustman; Charles M. Kinzig; Stephen Venetianer

[57] ABSTRACT

Compounds of formula (I) or a salt thereof:

(I)

in which $R^1$ is hydrogen, halogen, $C_{1-6}$alkyl, $C_{3-6}$cycloalkyl, $COC_{1-6}$alkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, acyl, nitro, trifluoromethyl, cyano, CHO, $SR^9$, $SOR^9$, $SO_2R^9$, $SO_2NR^{10}R^{11}$, $CO_2R^{10}$, $NR^{10}SO_2R^{11}$, $CONR^{10}R^{11}$, $CO_2NR^{10}R^{11}$, $CONR^{10}(CH_2)_pCO_2R^{11}$, $(CH_2)_pNR^{10}R^{11}$, $(CH_2)_pCONR^{10}R^{11}$, $(CH_2)_pNR^{10}COR^{11}$, $(CH_2)_pCO_2C_{1-6}$alkyl, $CO_2(CH_2)_pOR^{10}$, $CONHNR^{10}R^{11}$, $NR^{10}R^{11}$, $NR^{10}CO_2R^{11}$, $NR^{10}CONR^{10}R^{11}$, $CR^{10}=NOR^{11}$, $CNR^{10}=NOR^{11}$, where $R^{10}$ and $R^{11}$ are independently hydrogen or $C_{1-6}$alkyl and p is 1 to 4;

$R^2$ and $R^3$ are independently hydrogen, halogen, $C_{1-6}$alkyl, $C_{3-6}$cycloalkyl, $C_{3-6}$cycloalkenyl, $C_{1-6}$alkoxy, acyl, aryl, acyloxy, hydroxy, nitro, trifluoromethyl, cyano, hydroxy$C_{1-6}$alkyl, $C_{1-6}$alkylOC$_{1-6}$alkyl, $CO_2R^{10}$, $CONR^{10}R^{11}$, $NR^{10}R^{11}$ where $R^{10}$ and $R^{11}$ are independently hydrogen or $C_{1-6}$alkyl;

$R^4$ and $R^5$ are independently hydrogen or $C_{1-6}$alkyl;

$R^6$ is hydrogen, halogen, hydroxy, $C_{1-6}$alkyl or $C_{1-6}$alkoxy;

$R^7$ and $R^8$ are independently hydrogen, $C_{1-6}$alkyl, aralkyl, or together with the nitrogen atom to which they are attached form an optionally substituted 5–7-membered heterocyclic ring containing one or two heteroatoms selected from oxygen, nitrogen or sulphur;

A is oxygen, $S(O)_q$ where q is 0, 1 or 2, $CR^4=CR^5$ or $CR^4R^5$ where $R^4$ and $R^5$ are independently hydrogen or $C_{1-6}$alkyl, or A is $NR^{12}$ where $R^{12}$ is hydrogen or $C_{1-6}$alkyl;

B is $(CR^{13}R^{14})_q$ where q is 2, 3 or 4 and $R^{13}$ and $R^{14}$ are independently hydrogen or $C_{1-6}$alkyl or B is $(CR^{13}R^{14})_r$—D where r is 0, 1, 2 or 3 and D is oxygen, sulphur or $CR^{13}=CR^{14}$; m is 1 to 4; and n is 1 or 2, exhibit $5HT_{1D}$ antagonist activity.

12 Claims, No Drawings

BIPHENYLAMIDE COMPOUNDS AS 5HT$_{1D}$ ANTAGONISTS

This application is a 371 of PCT/BP95/03226 filed Aug. 14, 1995.

The present invention relates to novel amide derivatives, processes for their preparation, and pharmaceutical compositions containing them.

EPA 0 533 266/7/8 disclose a series of benzanilide derivatives which are said to possess 5HT$_{1D}$ receptor antagonist activity. Related compounds have also been disclosed in J Med Chem 1994, 37, 2253. These compounds are said to be of use in the treatment of various CNS disorders such as depression.

A structurally distinct class of compounds have now been discovered and have been found to exhibit 5HT$_{1D}$ antagonist activity. In a first aspect, the present invention therefore provides a compound of formula (I) or a salt thereof:

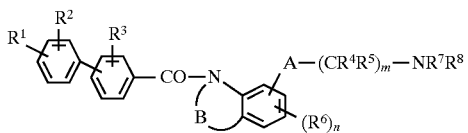

in which $R^1$ is hydrogen, halogen, $C_{1-6}$alkyl, $C_{3-6}$cycloalkyl, $COC_{1-6}$alkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, acyl, nitro, trifluoromethyl, cyano, CHO, $SR^9$, $SOR^9$, $SO_2R^9$, $SO_2NR^{10}R^{11}$, $CO_2R^{10}$, $NR^{10}SO_2R^{11}$, $CONR^{10}R^{11}$, $CO_2NR^{10}R^{11}$, $CONR^{10}(CH_2)_pCO_2R^{11}$, $(CH_2)_pNR^{10}R^{11}$, $(CH_2)_pCONR^{10}R^{11}$, $(CH_2)_pNR^{10}COR^{11}$, $(CH_2)_pCO_2C_{1-6}$alkyl, $CO_2(CH_2)_pOR^{10}$, $CONHNR^{10}R^{11}$, $NR^{10}R^{11}$, $NR^{10}CO_2R^{11}$, $NR^{10}CONR^{10}R^{11}$, $CR^{10}=NOR^{11}$, $CNR^{10}=NOR^{11}$, where $R^{10}$ and $R^{11}$ are independently hydrogen or $C_{1-6}$alkyl and p is 1 to 4;

$R^2$ and $R^3$ are independently hydrogen, halogen, $C_{1-6}$alkyl, $C_{3-6}$cycloalkyl, $C_{3-6}$cycloalkenyl, $C_{1-6}$alkoxy, acyl, aryl, acyloxy, hydroxy, nitro, trifluoromethyl, cyano, hydroxy$C_{1-6}$alkyl, $C_{1-6}$alkylOC$_{1-6}$alkyl, $CO_2R^{10}$, $CONR^{10}R^{11}$, $NR^{10}R^{11}$ where $R^{10}$ and $R^{11}$ are independently hydrogen or $C_{1-6}$alkyl;

$R^4$ and $R^5$ are independently hydrogen or $C_{1-6}$alkyl;

$R^6$ is hydrogen, halogen, hydroxy, $C_{1-6}$alkyl or $C_{1-6}$alkoxy;

$R^7$ and $R^8$ are independently hydrogen, $C_{1-6}$alkyl, aralkyl, or together with the nitrogen atom to which they are attached form an optionally substituted 5–7-membered heterocyclic ring containing one or two heteroatoms selected from oxygen, nitrogen or sulphur;

A is oxygen, $S(O)_q$ where q is 0, 1 or 2, $CR^4=CR^5$ or $CR^4R^5$ where $R^4$ and $R^5$ are independently hydrogen or $C_{1-6}$alkyl, or A is $NR^{12}$ where $R^{12}$ is hydrogen or $C_{1-6}$alkyl;

B is $(CR^{13}R^{14})_q$ where q is 2, 3 or 4 and $R^{13}$ and $R^{14}$ are independently hydrogen or $C_{1-6}$alkyl or B is $(CR^{13}R^4)_r$—D where r is 0, 1, 2 or 3 and D is oxygen, sulphur or $CR^{13}=CR^{14}$;

m is 1 to 4; and n is 1 or 2.

$C_{1-6}$alkyl groups, whether alone or as part of another group, may be straight chain or branched.

Suitably $R^1$ is hydrogen, halogen, $C_{1-6}$alkyl, $C_{3-6}$cycloalkyl, $COC_{1-6}$alkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, acyl, nitro, trifluoromethyl, cyano, CHO, $SR^9$, $SOR^9$, $SO_2R^9$, $SO_2NR^{10}R^{11}$, $CO_2R^{10}$, $NR^{10}SO_2R^{11}$, $CONR^{10}R^{11}$, $CO_2NR^{10}R^{11}$, $CONR^{10}(CH_2)_pCO_2R^{11}$, $(CH_2)_pNR^{10}R^{11}$, $(CH_2)_pCONR^{10}OR^{11}$, $(CH_2)_pNR^{10}COR^{11}$, $(CH_2)_pCO_2C_{1-6}$alkyl, $CO_2(CH_2)_pOR^{10}$, $CONHNR^{10}R^{11}$, $NR^{10}R^{11}$, $NR^{10}CO_2R^{11}$, $NR^{10}CONR^{10}R^{11}$, $CR^{10}=NOR^{11}$, $CNR^{10}=NOR^{11}$, where $R^{10}$ and $R^{11}$ are independently hydrogen or $C_{1-6}$alkyl and p is 1 to 4. Preferably $R^1$ is hydrogen, cyano, $COC_{1-6}$alkyl, $(CH_2)_pNR^{10}COR^{11}$ or $CR^{10}=NOR^{11}$. Most preferably $R^1$ is hydrogen, cyano, $COCH_3$, $CH_2NHCOCH_3$ or $CCH_3=NOCH_3$.

Suitably $R^2$ and $R^3$ are independently hydrogen, halogen, $C_{1-6}$alkyl, $C_{3-6}$cycloalkyl, $C_{3-6}$cycloalkenyl, $C_{1-6}$alkoxy, acyl, aryl, acyloxy, hydroxy, nitro, trifluoromethyl, cyano, hydroxy$C_{1-6}$alkyl, $C_{1-6}$alkylOC$_{1-6}$alkyl, $CO_2R^{10}$, $CONR^{10}R^{11}$, $NR^{10}R^{11}$ where $R^{10}$ and $R^{11}$ are independently hydrogen or $C_{1-6}$alkyl. Preferably $R^2$ is $C_{1-6}$alkyl, in particular methyl. Preferably $R^3$ is hydrogen.

Suitably $R^4$ and $R^5$ are independently hydrogen or $C_{1-6}$alkyl. Preferably $R^4$ and $R^5$ are both hydrogen.

Suitably $R^7$ and $R^8$ are independently hydrogen or $C_{1-6}$alkyl. Examples of $R^7$ and $R^8$ heterocyclic rings include morpholine, piperazine and piperidine. Optional substituents for such rings include $C_{1-6}$alkyl. Preferably $R^7$ and $R^8$ are both $C_{1-6}$alkyl, in particular methyl.

Suitably $R^6$ is hydrogen, halogen, hydroxy; $C_{1-6}$alkyl or $C_{1-6}$alkoxy. Preferably $R^6$ is $C_{1-6}$alkoxy such as methoxy or ethoxy. Most preferably $R^6$ is methoxy Suitably A is oxygen, $S(O)_q$ where q is 0, 1 or 2, $CR^4=CR^5$ or $CR^4R^5$ where $R^4$ and $R^5$ are independently hydrogen or $C_{1-6}$alkyl, or A is $NR^{12}$ where $R^{12}$ is hydrogen or $C_1$-alkyl. Preferably A is oxygen or $CR^4R^5$ such as $CH_2$. Most preferably A is oxygen.

Suitably B is $(CR^{13}R^{14})_q$ where q is 2, 3 or 4 and $R^{13}$ and $R^{14}$ are independently hydrogen or $C_{1-6}$alkyl or B is $(CR^{13}R^{14})_r$—D where r is 0, 1, 2 or 3 and D is oxygen, sulphur or $CR^{13}=CR^{14}$. Preferably B is $CH_2CH_2$.

Suitably m is 1 to 4, preferably m is 2

Suitably n is 1 or 2, preferably n is 1.

The groups —A$(CR^4R^5)_m$NR$^7R^8$ and $R^6$ can be attached to the phenyl ring at any suitable position. Preferably the group —A$(CR^4R^5)_m$NR$^7R^8$ is meta to the amide linkage and the group $R^6$ is para to the amide linkage. The groups $R^1$, $R^2$ and $R^3$ can be attached at any suitable position.

Particularly preferred compounds of the invention include:

1-(4'-Acetamidomethyl-2'-methylbiphenyl-4-carbonyl)-5-chloro-2,3-dihydro-6-(2-dimethylaminoethoxy)-1H-indole 1-(4'-Cyano-2'-methylbiphenyl-4-carbonyl)-2,3-dihydro-6-(2-dimethylaminoethoxy)-5-methoxy-1H-indole, 1-(4'-Acetyl-3'-methylbiphenyl-4-carbonyl)-2,3-dihydro-6-(2-dimethylaminoethoxy)-5-methoxy-1H-indole, 1-(4'-Acetyl-2'-methylbiphenyl-4-carbonyl)-6-(2-dimethylamino ethoxy)-5-methoxy-1H-indole, 1-(4'-Acetyl-3'-methylbiphenyl-4-carbonyl)-6-(2-dimethylamino ethoxy)-5-methoxy-1H-indole, 1-(4'-Cyano-2'-methylbiphenyl-4-carbonyl)-6-(2-dimethylaminoethoxy)-5-methoxy-1H-indole, 6-(2-Dimethylaminoethoxy)-5-methoxy-1-(4'-(1-(methoxyimino)ethyl)-2'-methylbiphenyl-4carbonyl)-1H-indole, 2,3-Dihydro-6-(2-dimethylaminoethoxy)-5-methoxy-1-(5'-methoxy carbonyl-2'-methylbiphenyl-4-carbonyl)-1H-indole, 6-(2-Dimethylaminoethoxy)-5-methoxy-1-(2-methylbiphenyl-4-carbonyl)-1H-indole, 1-(4'-Acetamidomethyl-2'-methylbiphenyl-4-carbonyl)-2,3-dihydro-6-(3-dimethylaminopropyl)-5-ethoxy-1H-indole, or pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers and mixtures thereof also form an aspect of the invention.

In a further aspect the present invention provides a process for the preparation of a compound of formula (I) which comprises.

(a) reaction of a compound of formula (II):

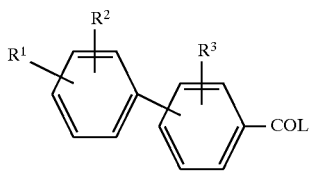

in which $R^1$, $R^2$ and $R^3$ are as defined in formula (I) and L is a leaving group with a compound of formula (III):

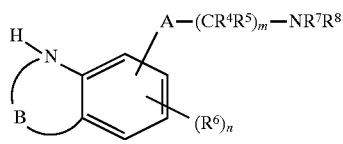

in which A, m, $R^4$, $R^5$, $R^6$, $R^7$, $R^8$ and n are as defined in formula (I), or (b) reaction of a compound of formula (III) as defined above with a compound of formula (IV):

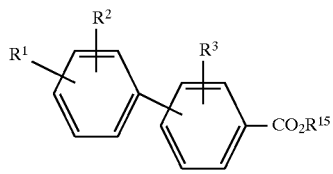

in which $R^1$, $R^2$ and $R^3$ are as defined in formula (I) and $R^{15}$ is $C_{1-6}$alkyl in the presence of a trialkylaluminium reagent; and optionally after any of the above processes in any order:

converting a compound of formula (I) into another compound of formula (I)

forming a pharmaceutically acceptable salt.

Suitable activated carboxylic acid derivatives of formula (II) include acyl halides and acid anhydrides. Activated compounds of formula (II) can also be prepared by reaction of the corresponding carboxylic acid with a coupling reagent such as carbonyldiimidazole, dicyclohexylcarbodiimide or diphenylphosphorylazole. Preferably the group L is halo, particularly chloro.

A compound of formula (II) is typically reacted with a compound of formula (III) in an inert organic solvent such as DMF, THF or dichloromethane at ambient or elevated temperature in the presence of a base such as triethylamine, pyridine or an aqueous alkali metal hydroxide. When the compound of formula (III) is an indole, t-BuOK can also be used in an inert solvent such as THF.

Compounds of formula (II) can be prepared from a compound of formula (V):

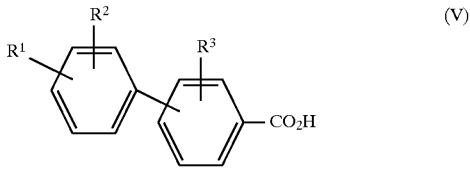

in which $R^1$, $R^2$ and $R^2$ are as defined in formula (I) using standard procedures. For example acid chlorides can be prepared by reaction with phosphorous pentachloride, oxalyl chloride or thionyl chloride. Acid anhydrides can be prepared by reaction with a suitable acid anhydride, for example trifluoroacetic anhydride.

Compounds of formula (III) can be reacted with compounds of formula (IV) in an organic solvent such as toluene in an inert atmosphere in the presence of a trialkylaluminium reagent, for example trimethylaluminium.

Intermediate compounds of formulae (III) and (IV) are commercially available or can be prepared using standard procedures such as those outlined in EPA 533266/7/8. Certain intermediate compounds of formulae (II), (III) and (IV) are novel and form a further aspect of the invention.

It will be appreciated to those skilled in the art that it may be necessary to protect certain reactive substituents during some of the above procedures. Standard protection and deprotection techniques can be used. For example, primary amines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals, thioacetals or thioketals. Deprotection is achieved using standard conditions.

Certain compounds of formula (I) can be converted into further compounds of formula (I). For example compounds in which $R^7$ and $R^8$ are both hydrogen or one of $R^7$ or $R^8$ is hydrogen and the other is $C_{1-6}$alkyl can be converted to compounds in which $R^7$ and $R^8$ are both $C_{1-6}$alkyl using standard alkylation techniques.

$5HT_{1D}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder, memory disorders, including dementia, amnestic disorders and age-associated memory impairment; and disorders of eating behaviours, including anorexia nervosa and bulimia nervosa. Other CNS disorders include motor disorders such as Parkinson's disease, dementia in Parkinson's disease, neuroleptic-induced Parkinsonism and tardive dyskinesias, as well as other psychiatric disorders.

$5HT_{1D}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction. Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression. It will be appreciated by those skilled in the art that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Examples illustrate the preparation of compounds of the invention.

Description 1
4'-Acetamidomethyl-2'-methylbiphenyl-4-carboxylic acid

4-Bromo-3-methylbenzylamine (EP 532266) (7.36 g, 0.037 mol) was dissolved in 1,2-dimethoxyethane (DME) (180 ml), with stirring, and was treated with 4-carboxyphenyl boronic acid (6.14 g, 0.037 mol), followed by a solution of sodium carbonate (17.65 g, 0.167 mol) in water (180 ml). The reaction mixture was then flushed with argon and tetrakistriphenylphosphinepalladium (O) (1.00 g) was added. The reaction mixture was then heated to reflux under argon. After 16 h, the reaction mixture was allowed to cool and the DME was removed by evaporation under reduced pressure. The aqueous residue was then diluted with water (~200 ml) and extracted with EtOAc (2×150 ml). The aqueous layer was then treated with acetic anhydride (6.98 ml, 0.074 mol) and stirred for 1 h at room temperature. The resulting pale brown solution was then filtered through kieselguhr to give a pale yellow solution which was acidified to pH5 using conc. HCl to give an off white precipitate which was filtered off, washed with water and dried in vacuo to give the title compound as an off white solid (5.85 g, 56%).

$^1$H NMR (200 MHz, $CD_3SOCD_3$) δ; 8.45 (t, 1H), 7.95 (d, 2H), 7.32 (d, 2H), 7.15 (m, 3H), 4.28 (d, 2H), 2.20 (s, 3H), 1.90 (s, 3H)

Description 2
Methyl 4'-acetamidomethyl-2'-methylbiphenyl-4-carboxylate

Thionyl chloride (0.119 ml, 1.63 mmol) was added dropwise to MeOH (5 ml) at 0° C., followed by a solution of 4'-acetamidomethyl-2'-methylbiphenyl-4-carboxylic acid (D1, 0.345 g, 1.22 mmol) in MeOH (10 ml). The mixture was heated under reflux for 1.5 hr and the solvent removed in vacuo. The residue was dissolved in $CH_2Cl_2$ (30 ml) and washed with aq. $Na_2CO_3$ followed by water. The organic extract was dried ($Na_2SO_4$) and concentrated in vacuo to give a colourless oil which purified by column chromatography on silica gel eluting with EtOAc to give a colourless oil that crystallised on standing (0.242 g, 68%).

$^1$H NMR ($CDCl_3$) δ: 8.1 (d, 2H), 7.38 (d, 2H), 7.14–7.23 (m, 3H), 5.80–5.90 (bs, 1H), 4.45 (d, 2H), 3.90 (s, 3H), 2.28 (s, 3H), 2.05 (s, 3H)

Description 3
2-Chloro-5-nitroanisole

The title compound was prepared from 2-methoxy-4-nitroaniline (15.0 g, 0.089 mol) using a literature procedure (Bonilha, J. B. S. et al., Tetrahedron 1993, 49(15), 3053–64). Yield 8.61 g, (51%).

$^1$H NMR ($CDCl_3$) δ: 7.45–7.90(m, 3H), 4.0 (s, 3H)

Description 4
2-Chloro-5-nitrophenol

The title compound was synthesised from 2-chloro-5-nitroanisole (D3, 6.0 g, 0.032 mol) using the method described in Tetrahedron, 1993, 49(15), 3053–64. Yield 5.08 g, (91%).

Description 5
4-Chloro-3-(2-dimethylaminoetboxy)nitrobenzene

2-Chloro- 5-nitrophenol (D4, 350 mg, 0.002 mol) in DME (25 ml) was treated with dimethylaminoethyl chloride HCl (640 mg) and $K_2CO_3$ (5 g) and the mixture was heated under reflux for 19 hours. The reaction was allowed to cool to room temperature, then the solvent removed in vacuo. The residue was taken up in water and extracted with EtOAc. The organic layers were combined, dried ($Na_2SO_4$) and concentrated in vacuo to give a yellow oil, which crystallised on standing. Purification by flash column chromatography, eluting with EtOAc, gave the title compound (343 mg, 70% ).

$^1$H NMR ($CDCl_3$) δ: 7.81 (m, 2H ) 7.60 (m, 1H ), 4.21 (t, 2H), 2.88 (t, 2H), 2.40 (s, 6H)

Description 6
4-Chloro-3-(2-dimethylaminoethoxy)aniline

To 4-chloro-3-(2-dimethylaminoethoxy)nitrobenzene (D5, 1.5 g, 0.006 mol) in EtOH (25 ml) at 60° C., was added $SnCl_2$ (4.2 g) in concentrated hydrochloric acid (7.6 ml) dropwise. The mixture was then heated under reflux for 30 mins and after cooling to room temperature, diluted with water (50 ml), and basified by addition of 40% aq. sodium hydroxide.

The mixture was extracted into $CH_2Cl_2$ and the combined organic layers, dried ($Na_2SO_4$) and concentrated in vacuo to give the title compound as a brown oil (1.22 g , 93%).

$^1$H NMR ($CDCl_3$) δ: 7.08 (d, 1H ), 6.24-6.18 (m,2H), 4.03 (t, 2H), 3.78 (brs, 2H), 2.77 (t, 2H), 2.34 (s, 6H)

Description 7
N-[4-Chloro-3-(2-dimethylaminoethoxy)phenyl] aminoacetaldehyde dimethyl acetal To a suspension of 4-chloro-3-(2-dimethylaminoethoxy) aniline (D6, 1.22 g, 0.006 mol) in McOH (30 ml) containing dimethoxyethanal in MTBE (1.76 g, 0.17 mol) and glacial acetic acid (1.71 g) was added sodium cyanoborohydride (1.78 g, 0.03 mol) portionwise at 0 C. After addition, the reaction was left to stir at room temperature for 1 hour, and then 10% aqueous NaOH was added and the mixture was extraced with $CH_2Cl_2$ and the combined organic layers were dried ($Na_2SO_4$), and concentrated in vacuo to give a brown oil. Purification by FCC, eluting with $CH_2Cl_2$ gave the title compound (1.49 mg, 87% )

$^1$H NMR ($CDCl_3$) δ: 7.10 (d, 1H), 6.21-6.12 (m, 2H), 4.53 (t, 1H), 4.10 (t, 2H ), 3.92-3.87 (m, 1H), 3.4 (s, 6H), 3.21 (t, 2H), 2.80 (t , 2H), 2.38 (s, 6H).

Description 8
5-Chloro-6-(2-dimethylaminoethoxy)-1H-indole

A solution of N-[4-chloro-3-(2-dimethylaminoethoxy) phenyl]aminoacetaldehyde dimethyl acetal (D7, 0.61 g, 0.002 mol) in TFA (2.6 ml) at 0° C., was treated with TFAA (2.6 ml) under an argon atmosphere. More TFA (3.7 ml ) was added and the reaction was heated to reflux for 48 h. The solution was evaporated to dryness and the residue taken up in EtOAc. The extract was dried ($Na_2SO_4$) and concentrated in vacuo to leave a brown oil which was dissolved in MeOH (10 ml), treated with $K_2CO_3$ (1 g) and then stirred at room temperature for 3 h The mixture was concentrated in vacuo, and then the residue treated with water and extracted with EtOAc. The solution was dried ($Na_2SO_4$) and concentrated in vacuo to give the title compound as a brown solid (0.37 g , 76%)

$^1$H NMR ($CDCl_3$) δ: 8.32 (brs, 1H), 7.6 (s, 1H), 7.12 (m, 1H), 6.92 (s, 1H), 6.47 (m, 1H), 4.11 (t, 2H), 2.81 (t, 2H), 2.40 (s, 6H)

Description 9
5-Chloro-2,3-dihydro-6-(2-dimethylaminoethoxy)-1H-indole

5-Chloro-6-(2-dimethylaminoethoxy)-1H-indole (D8, 0.2 g, 0.008 mol) in glacial acetic acid (5 ml) was treated with sodium cyanoborohydride (0.25 g, 0.004 mol ) at room temperature with stirring for 1 h. The mixture was diluted with water and basified with 10% aq NaOH. The product was extracted into $CH_2Cl_2$, and the combined extracts dried ($Na_2SO_4$) and concentrated in vacuo to give the title compound as a brown oil (0.21 g, 100%)

$^1$H NMR ($CDCl_3$) δ: 7.04 (s, 1H), 6.30 (s, 1H), 4.04 (t, 2H), 3.59 (t, 2H), 2.98 (t, 2H), 2.79 (t, 2H), 2.38 (s, 6H)

Description 10
2-(2-Dimethylaminoethoxy)-4-nitroanisole

A stirred solution of 2-methoxy-5-nitrophenol (10 g, 0.059 mole) in 1,2-dimethoxyethane (80 ml) was treated with saturated aqueous potassium carbonate solution (32 ml) followed by 2-dimethylaminoethyl chloride hydrochloride (8.2 g, 0.057 mole) and heated under reflux for 17 hours. A further quantity of 2-dimethylaminoethyl chloride hydrochloride (4.0 g, 0.029 mole) was added and reflux was continued for 18 hours. The mixture was then concentrated in vacuo and the residue treated with 10% $Na_2CO_3$ solution (100 ml) and extracted with ethyl acetate (2×100 ml). The combined extract was dried ($Na_2SO_4$) and concentrated in vacuo to afford the title compound as a yellow solid (11.8 g, 83%).

$^1$H NMR ($CDCl_3$) δ: 7.92 (dd, 1H), 7.77 (d, 1H), 6.91 (d, 1H), 4.18 (t, 2H), 3.96 (s, 3H), 2.82 (t, 2H), 2.37 (s, 6H)

Description 11
3-(2-Dimethylaminoethoxy)-4-methoxyaniline

A solution of 2-(2-dimethylaminoethoxy)-4-nitroanisole (D10, 11.8 g, 0.049 mole) in ethanol (200 ml) was hydrogenated over 10% Pd-C (1 g) at atmospheric temperature and pressure. The catalyst was filtered off through kieselguhr and the filtrate concentrated in vacuo to afford the title compound as a beige solid (10.3 g, 100%).

$^1$H NMR ($CDCl_3$) δ: 6.71 (d, 1H), 6.33 (d, 1H), 6.24 (dd, 1H), 4.07 (t, 2H), 3.78 (s, 3H), 3.46 (br s, 2H), 2.76 (t, 2H), 2.33 (s, 6H).

Description 12
N-[3-(Dimethylaminoethoxy)-4-methoxyphenyl]amino acetaldehyde dimethyl acetal A solution of 3-(2-dimethylaminoethoxy)-4-methoxyaniline (D11, 5.7 g, 0.027 mole) ethanol (120 ml) was treated with a solution of 2,2-dimethoxyacetaldehyde in methyl tert-butyl ether (9.5 g of approx. 40% solution, 0.036 mole) and kept at room temperature for 16 hours. The solution was then hydrogenated over 10% Pd-C (0.6 g) at atmospheric pressure and temperature for 7 hours. The catalyst was removed by filtration through kieselguhr and the filtrate concentrated in vacuo. The residue was dissolved in ethyl acetate (100 ml), washed twice with water (2×60 ml), then dried ($Na_2SO_4$) and concentrated in vacuo. The residue was chromatographed on silica gel eluting with 5% methanol/chloroform to afford the title compound as a red oil (5.4 g, 67%).

$^1$H NMR ($CDCl_3$) δ: 6.75 (d, 1H), 6.30 (d, 1H), 6.19 (dd, 1H), 4.56 (t, 1H), 4.08 (t, 2H), 3.78 (s, 3H), 3.61 (br t, 1H), 3.42 (s, 6H), 3.20 (t, 2H), 2.78 (t, 2H), 2.34 (s, 6H)

Description 13
6-(2-Dimethylaminoethoxy)-5-methoxy-1H-indole

A stirred solution of N-[3-(2-dimethylaminoethoxy)4-methoxyphenyl]aminoacetaldehyde dimethyl acetal (D12, 5.3 g, 0.018 mole) in trifluoroacetic acid (22 ml) at −5° C. under argon was treated dropwise over 40 minutes with trifluoroacetic anhydride (22 ml). After a further 30 minutes the dark solution was treated with more trifluoroacetic acid (33 ml) and then heated under reflux for 7 hours. The solution was concentrated in vacuo and the residue basified with 10% $Na_2CO_3$ solution and extracted with ethyl acetate. The extract was dried ($Na_2SO_4$), concentrated in vacuo and the residue dissolved in methanol (100 ml), treated with potassium carbonate (10 g) and stirred at room temperature for 3 hours. The mixture was concentrated in vacuo,.the residue treated with water (60 ml) and extracted with ethyl acetate (2×70 ml). The combined extract was dried ($Na_2SO_4$) and concentrated in vacuo to afford the title compound as a brown solid (3.5 g, 83%).

$^1$H NMR ($d^6$DMSO) δ: 7.14 (t, 1H), 7.05 (s, 1H), 6.96 (s, 1H), 6.27 (br t, 1H), 4.03 (t, 2H), 3.75 (s, 3H), 3.45 (br s), 2.70 (t, 2H), 2.27 (s, 6H).

Description 14
2,3-Dihydro-6-(2-dimethylaminoethoxy)-5-methoxy-1H-indole

A stirred solution of 6-(2-dimethylaminoethoxy)-5-methoxy-1H-indole (D13, 0.50 g, 2.1 mmole) in glacial acetic acid (10 ml) at room temperature was treated portionwise over 15 minutes with sodium cyanoborohydride (0.25 g, 4.0 mmole). After 2 hours the solution was diluted with water (50 ml), basified by addition of $Na_2CO_3$ and then extracted with ethyl acetate (2×50 ml). The combined extract was dried ($Na_2SO_4$), and concentrated in vacuo to leave the title compound as a brown oil (0.37 g, 73%).

$^1$H NMR (CDCl$_3$) δ: 6.75 (s, 1H), 6.37 (s, 1H), 4.05 (t, 2H), 3.90 (br s, 1H), 3.77 (s, 3H), 3.52 (t, 2H), 2.96 (t, 2H), 2.73 (t, 2H), 2.32 (s, 6H).

Description 15
4'-Cyano-2'-methylbiphenyl-4-carboxylic acid

A stirred solution of 4-bromo-3-methylbenzonitrile (5.0 g, 0.026 mole) and 4-boronobenzoic acid (4.2 g, 0.026 mole) in a mixture of DME (100 ml) and water (100 ml) under argon was treated with sodium carbonate (11.6 g, 0.11 mole) and tetrakis (triphenylphosphine) palladium (O) (0.55 g) and heated under reflux for 20 h. The solution was concentrated in vacuo to approx. 100 ml volume, then washed with ethyl acetate and acidified with 5M HCl acid. The solid which was produced was filtered off, washed with water and dried in vacuo to afford the title compound as a white solid (4.16 g, 69%).

$^1$H NMR (250 MHz, $d^6$DMSO) δ (ppm): 8.03 (d, 2H), 7.82 (d, 1H), 7.74 (dd, 1H), 7.49 (d, 2H), 7.43 (d, 1H), 2.26 (s, 3H).

Description 16
N-Methoxy-N-methyl-4-bromo-3-methylbenzamide

A stirred suspension of 4-bromo-3-methylbenzoic, acid (5.0 g, 0.023 mole) in thionyl chloride (20 ml) was heated under reflux for 2 hours, then concentrated in vacuo. The residual acid chloride was dissolved in dichloromethane (100 ml) and added dropwise over 10 minutes to a stirred solution of N,O-dimethylhydroxylamine hydrochloride (2.4 g, 0.025 mole) and pyridine (5.6 ml, 0.069 mole) in dichloromethane (150 ml) and acetonitrile (20 ml) at −20° C. The reaction mixture was allowed to warm to room temperature over 3 hours then treated with 10% $Na_2CO_3$ solution and extracted with dichloromethane. The extract was dried ($Na_2SO_4$) and concentrated in vacuo to afford the title compound as a pale yellow oil (5.9 g, 100%).

$^1$H NMR (200 MHz, CDCl$_3$) δ (ppm): 7.60-7.50 (m, 2H), 7.37 (dd, 1H), 3.54 (s, 3H), 3.35 (s, 3H), 2.42 (s, 3H)

Description 17
4-Bromo-3-methylacetophenone

A solution of N-methoxy-N-methyl-4-bromo-3-methylbenzamide (D16, 1.50 g, 0.0057 mole) in dry ether (30 ml) was added dropwise over 10 minutes to a stirred solution of methylmagnesium iodide (0.007 mole) in dry ether (15 ml) under argon. The mixture was then heated under reflux for 1 hour, allowed to cool and poured into well stirred 1M HCl (50 ml). The mixture was extracted with ethyl acetate and the extract washed with 10% $Na_2CO_3$ solution, dried ($Na_2SO_4$) and concentrated in vacuo to afford the title compound as a pale yellow oil (1.14 g, 94%).

$^1$H NMR (250 MHz, CDCl$_3$) δ (ppm): 7.81 (s, 1H), 7.62 (s, 2H), 2.57 (s, 3H), 2.45 (s, 3H).

Description 18
4'-Acetyl-2'-methylbiphenyl-4-carboxylic acid

The title compound was prepared from 4-bromo-3-methylacetophenone (D17) using a similar procedure to Description 15 as a white solid (80%).

$^1$H NMR (250 MHz, CDCl$_3$) δ (ppm): 8.13 (d, 2H), 7.89 (s, 1H), 7.84 (d, 1H), 7.40 (d, 2H), 7.33 (d, 1H), 2.65 (s, 3H), 2.33 (s, 3H).

Description 19
N-Methoxy-N-methyl-4-bromo-2-methylbenzamide

The title compound was prepared from 4-bromo-2-methylbenzoic acid using a similar procedure to Description 16 as a yellow oil (100%).

$^1$H NMR (250 MHz, CDCl$_3$) δ (ppm): 7.38 (s, 1H), 7.35 (dd, 1H), 7.14 (d, 1H), 3.50 (br s, 3H), 3.31 (br s, 3H), 2.31 (s, 3H).

Description 20
4-Bromo-2-methylacetophenone

The title compound was prepared from N-methoxy-N-methyl-4-bromo-2-methylbenzamide (D19) using a similar procedure to Description 17 as a colourless oil (69%).

$^1$H NMR (200 MHz, CDCl$_3$) δ (ppm): 7.57 (d, 1H), 7.46-7.37 (m, 2H), 2.56 (s, 3H), 2.50 (s, 3H).

Description 21
4'-Acetyl-3'-methylbiphenyl-4-carboxylic acid

The title compound was prepared from 4-bromo-2-methylacetophenone (D20) using a similar procedure to Description 15 as a pale yellow solid (42%).

$^1$H NMR (250 MHz, CDCl$_3$) δ (ppm): 11.7 (br s, 1H), 8.05 (s, 1H), 8.00 (d, 1H), 7.80 (d, 1H), 7.32 (d, 1H), 7.28-7.20 (m, 2H), 2.65 (s, 3H), 2.61 (s, 3H), 2.34 (s, 3H).

Description 22
5'-Methoxycarbonyl-2'-methylbiphenyl-4-carboxylic acid

A stirred solution of methyl 3-bromo-4-methylbenzoate (2.6 g, 0.011 mole) in dry DMF (20 ml) under argon was treated with 4-boronobenzoic acid (1.85 g, 0.011 mole) and tetrakis (triphenylphosphine) palladium (O) (400 mg), followed by triethylamine (4.68 ml, 0.046 mole). The mixture was heated at 100° C. for 18 hours, then concentrated in vacuo. The residue was treated with ethyl acetate and extracted with 10% $NaHCO_3$ solution. The basic extract was acidified with dil. HCl and extracted with ethyl acetate. The extract was dried ($Na_2SO_4$) and concentrated in vacuo to afford the title compound as a light orange solid (2.12 g, 85%).

$^1$H NMR (250 MHz, $d^6$DMSO) δ (ppm): 13.1 (br s, 1H), 8.09-8.00 (m, 2H), 7.92-7.75 (m, 2H), 7.68-7.43 (m, 3H), 3.88 (s, 3H), 2.30 (s, 3H).

Description 23
2-Methylbiphenyl-4-carboxylic acid

The title compound was prepared from 4-bromo-3-methylbenzoic acid and benzeneboronic acid using a similar procedure to Description 15, as a pale yellow solid (89%).

$^1$H NMR (200 MHz, $d^6$DMSO) δ (ppm): 13.0 (br s, 1H), 7.91 (s, 1H), 7.84 (dd, 1H), 7.57-7.30 (m, 6H), 2.30 (s, 3H).

Description 24
2-Chloro-5-nitro-N,N-dimethylcinnamide

A stirred suspension of 2-chloro-5-nitrocinnamic acid (20 g, 0.088 mol) in thionyl chloride (100 ml) was heated to reflux for 3 h, then concentrated in vacuo to leave the acid chloride as a beige solid. This was dissolved in a mixture of $CH_2Cl_2$ (100 ml) and dry ThF (30 ml), then added dropwise to a stirred suspension of dimethylamine hydrochloride (9.8 g, 0.12 mol) and pyridine (24 ml) at $-20°$ C. under argon. The reaction mixture was then allowed to warm to room temperature and stirred for 1.5 h. The solvent was removed in vacuo and the residue redissolved in $CH_2Cl_2$. The resulting solution was washed with 10% aq. $Na_6CO_3$ solution, 1M HCl acid, then water, then dried ($Na_2CO_3$) and concentrated in vacuo to give the title compound as a beige solid (22.2 g, 99%).

$^1$H NMR (250 MHz, $CDCl_3$) δ (ppm): 8.46 (d, 1H), 8.12 (dd, 1H), 8.00 (d, 1H), 7.60 (d, 1H), 7.04 (d, 1H), 3.23 (s, 3H), 3.11 (s, 3H)

Description 25
2-Ethoxy-5-nitro-N,N-dimethylcinnamide

A stirred suspension of freshly prepared sodium ethoxide (0.058 mole) in dry DMF (75 ml) at 0° C. under argon was treated dropwise over 5 minutes with a solution of 2-chloro-5-nitro-N,N-dimethylcinnamide (D24) (10 g, 0.039 mole) in dry DMF (60 ml). The reaction mixture was allowed to warm to room temp. over 1 h, then poured into 1M HCl acid/ice (1000 ml) with stirring. The precipitate which formed was filtered off, washed with water and dried to afford the title compound as a beige solid (9.36 g, 91%).

$^1$H NMR (200 MHz, $CDCl_3$) δ (ppm): 8.42 (d, 1H), 8.20 (dd, 1H), 7.93 (d, 1H), 7.09 (d, 1H), 6.96 (d, 1H), 4.21 (q, 2H), 3.19 (br s, 3H), 3.10 (br s, 3H), 1.52 (t, 3H).

Description 26
3-(5-Amino-2-ethoxyphenyl)-N,N-dimethylpropionamide

A stirred solution of 2-ethoxy-5-nitro-N,N-dimethylcinnamide (D25) (9.36 g, 0.035 mole) in ethanol (250 ml) was hydrogenated over 10% Pd-C (1 g) at atmospheric pressure and temp. for 4 h. The catalyst was removed by filtration through kieselguhr and the filtrate concentrated in vacuo to afford the title compound as a brown oil (8.36 g, 100%).

$^1$H NMR (200 MHz, $CDCl_3$) δ (ppm): 6.68 (d, 2H), 6.61 (d, 1H), 6.54 (dd, 1H), 3.95 (q, 2H), 3.46 (br s, 2H), 2.97 (s, 3H), 2.94 (s, 3H), 2.92-2.79 (m, 2H), 2.65-2.50 (m, 2H), 1.36 (t, 3H).

Description 27
3-(3-Dimethylaiminopropyl)-4-ethoxyaniline

A solution of 3-(5-amino-2-ethoxyphenyl)-N,N-dimethylpropionamide (D26) (8.4 g, 0.035 mole) in THF (90 ml) was added dropwise over 15 mins to a stirred suspension of lithium aluminium hydride (2.0 g, 0.056 mole) in THF (150 ml) at 0° C. under argon. The mixture was then allowed to warm to room temp. and stir for 1.5 h. The mixture was treated carefully with water (2.0 ml), then 10% NaOH solution (2.0 ml), followed by water again (6.0 ml). The mixture was filtered through kieselguhr and the filtrate concentrated in vacuo to afford the title compound as a brown oil (6.68 g, 85%).

$^1$H NMR (250 MHz, $CDCl_3$) δ (ppm): 6.66 (d, 1H), 6.55-6.44 (m, 2H), 3.93 (q, 2H), 3.37 (br s, 2H), 2.60-2.50 (m, 2H), 2.35-2.25 (m, 2H), 2.22 (s, 6H), 1.83-1.68 (m, 2H), 1.36 (t, 3H).

Description 28
6-(3-Dimethylaminopropyl)-5-ethoxy-1H-indole

The title compound was prepared from 3-(3-dimethylaminopropyl)-4-ethoxyaniline (D27) using similar procedures to Descriptions 12 and 13 but with a reflux time of 19 h for the cyclisation (8%).

$^1$H NMR (200 MHz, $CDCl_3$) δ (ppm): 8.46 (br s, 1H), 7.13 (s, 1H), 7.09 (t, 1H), 7.03 (s, 1H), 6.42 (t, 1H), 4.06 (q, 2H), 2.78-2.68 (m, 2H), 2.44-2.32 (m, 2H), 2.25 (s, 6H), 1.95-1.74 (m, 2H), 1.44 (t, 3H).

Description 29
2,3-Dihydro-6-(3-dimethylaminopropyl)-5-ethoxy-1H-indole

The title compound was prepared from 6-(3-dimethylaminopropyl)-5-ethoxy-1H-indole (D28) using a similar procedure to Description 14 (100%).

$^1$H NMR (200 MHz, $CDCl_3$) δ (ppm): 6.72 (s, 1H), 6.48 (s, 1H), 6.05 (br s, 1H), 3.96 (q, 2H), 3.50 (t, 2H), 2.98 (t, 2H), 2.84-2.72 (m, 2H), 2.68-2.50 (m, 2H), 2.62 (s, 6H), 2.00-1.80 (m, 2H), 1.36 (t, 3H).

EXAMPLE 1
1-(4'-Acetamidomethyl-2'-methylbiphenyl-4-carbonyl)-5-chloro-2,3-dihydro-6-(2-dimethylaminoethoxy)-1H-indole The product from description 9 (0.125 g, 0.52 mmol) was dissolved in toluene (5 ml) and the solution treated with $Me_3Al$ (1.04 ml of a 2.0M solution in hexane, 2.08 mmol) under an atmosphere of argon. After 0.25 hr a solution of the product from description 2 (0.162 g, 0.546 mmol) in toluene (5 ml) was added. The mixture was then heated to 80° C. After 4 hr, the reaction mixture was allowed to cool and was left at room temperature for 18 hr before being poured onto a slurry of silica gel (10 g) in $CH_2Cl_2$ (30 ml). The mixture was then stirred until effervescence ceased (0.5 hr). The mixture was filtered and the silica gel pad washed with a mixture of $CH_2Cl_2$:MeOH (80:20). The filtrate was concentrated in vacuo to give a yellow oil which was purified by column chromatography on silica gel eluting with $CH_2Cl_2$:MeOH (90:10) to give a pale yellow oil (0.173 g, 74%).

$^1$H NMR ($CDCl_3$) δ: 7.60 (d, 2H), 7.36 (d, 2H), 7.15–7.22 (m, 5H), 5.75–5.85 (bs, 1H), 4.46 (d, 2H) 4.05–4.20 (m, 4H), 3.08 (t, 2H), 2.70–2.85 (m, 2H), 2.38 (s, 6H), 2.28 (3H), 2.05 (3H)

EXAMPLE 2
1-(4'-Cyano-2'-methylbiphenyl-4-carbonyl)-2,3-dihydro-6-(2-dimethylaminoethoxy)-5-methoxy-1H-indole A suspension of 4'-cyano-2'-methylbiphenyl-4-carboxylic acid (D15, 0.50 g, 2 mmole) in dichloromethane (10 ml) was treated with oxalyl chloride (0.2 ml, 2.2 mnmole) and DMF (1 drop) and stirred at room temp. for 2 h, then concentrated in vacuo to leave the acid chloride as a yellow solid. This was dissolved in dichloromethane (5 ml) and added to a stirred solution of 2,3-dihydro-6-(2-dimethylaminoethoxy)-5-methoxy-1H-indole (D14, 0.50 g, 2 mmole) and triethylamine (0.6 ml, 4 mmole) in dichloromethane (10 ml). The reaction mixture was stirred for 18 h at room temp., then treated with sat. $NaHCO_3$ solution and extracted with dichloromethane. The extract was dried ($Na_2SO_4$) and concentrated in vacuo to leave a brown oil, which was chromatographed on silica gel eluting with 0–5% methanol/dichloromethane to afford the title compound as a yellow solid mp 167°–171° C. (0.32 g, 33%).

$^1$H NMR (250 MHz, $CDCl_3$) δ (ppm): 8.01 (br s, 1H - low integration), 7.69-7.52 (m, 4H), 7.42-7.30 (m, 3H), 6.76 (s, 1H), 4.30-4.02 (br m, 4H), 3.85 (s, 3H), 3.08 (t, 2H), 2.83 (br s, 2H), 2.37 and 2.31 (br s and s, together 9H).

EXAMPLE 3
1-(4'-Acetyl-3'-methylbiphenyl-4-carbonyl)-2,3-dihydro-6-(2-dimethylaminoethoxy)-5-methoxy-1H-indole The title compound was prepared from 4'-acetyl-3'-methylbiphenyl-4-carboxylic acid (D21) and 2,3-dihydro-6-(2-dimethylaminoethoxy-5-methoxy-1H-indole (D14) using a similar procedure to Example 2 as a yellow solid mp 160°–162° C. (47%).

$^1$H NMR (200 MHz, CDCl$_4$) δ (ppm): 8.00 (br s, 1H - low integration), 7.83 (d, 1H), 7.78-7.60 (m, 4H), 7.57-7.47 (m, 2H), 6.78 (s, 1H), 4.3-4.0 (br, 4H), 3.84 (s, 3H), 3.09 (t, 2H), 2.85 (br, 2H), 2.62 (s, 6H), 2.40 (br s, 6H).

EXAMPLE 4
1-(4'-Acetyl-2'-methylbiphenyl-4-carbonyl)-6-(2-dimethylaminoethoxy)-5-methoxy-1H-indole A suspension of 4'-acetyl-2'-methylbiphenyl-4-carboxylic acid (D118, 0.40 g, 1.5 mmole) in dichloromethane (13 ml) was treated with oxalyl chloride (0.13 ml, 1.6 mmole) and DMF (1 drop) and stirred at room temp. for 2 h, then concentrated in vacuo to leave the acid chloride. A stirred solution of 6-(2-dimethylaminoethoxy)-5-methoxy-1H-indole (D13, 0.35 g, 1.5 mmole) in dry THF (13 ml) under argon was treated with potassium t-butoxide (0.17 g, 1.5 mmole) and stirred at room temp. for 20 minutes, then treated with a solution of the above acid chloride in THF (5 ml). The reaction mixture was stirred at room temp. for 64 h, then treated with sat. NaHCO$_3$ solution and extracted with dichloromethane. The extract was dried (Na$_2$SO$_4$) and concentrated in vacuo to leave a brown oil, which was chromatographed on silica gel eluting with 0–5% methanol/dichloromethane to afford the title compound as a light brown oil (0.38 g, 62%). Oxalate salt mp 210°–215° C.

$^1$H NMR (free base) (200 MHz, CDCl$_3$) δ (ppm): 8.15 (s, 1H), 7.95-7.79 (m, 4H), 7.50 (d, 2H), 7.37 (d, 1H), 7.23 (d, 1H), 7.05 (s, 1H), 6.55 (d, 1H), 4.25 (t, 2H), 3.93 (s, 3H), 2.91 (t, 2H), 2.65 (s, 3H), 2.42 (s, 6H), 2.38 (s, 3H).

EXAMPLE 5
1-(4'-Acetyl-3'-methylbiphenyl-4-carbonyl)-6-(2-dimethylaminoethoxy)-5-methoxy-1H-indole The title compound was prepared from 4'-acetyl-3'-methylbiphenyl-4-carboxylic acid (D21) and 6-(2-dimethylaminoethoxy)-5-methoxy-1H-indole (D13) using a similar procedure to Example 4 as an off-white solid mp 125°–127° C. (36%).

$^1$H NMR (200 MHz, CDCl$_3$) δ (ppm): 8.15 (s, 1H), 7.85-7.70 (m, 5H), 7.57-7.50 (m, 2H), 7.20 (d, 1H), 7.05 (s, 1H), 6.52 (d, 1H), 4.23 (t, 2H), 3.92 (s, 3H), 2.88 (t, 2H), 2.62 (s, 6H), 2.40 (s, 6H).

EXAMPLE 6
1-(4'-Cyano-2'-methylbiphenyl-4-carbonyl)-6-(2-dimethylaminoethoxy)-5-methoxy-1H-indole The title compound was prepared from 4'-cyano-2'-methylbiphenyl-4-carboxylic acid (D15) and 6-(2-dimethylaminoethoxy)-5-methoxy-1H-indole (D13) using a similar procedure to Example 4 as a white solid mp 140°–142° C. (42%).

$^1$H NMR (250 MHz, CDCl$_3$) δ (ppm): 8.15 (s, 1H), 7.82 (d, 2H), 7.58 (d, 2H), 7.48 (d, 2H), 7.38 (d, 1H), 7.22 (d, 1H), 7.08 (s, 1H), 6.55 (d, 1H), 4.28 (t, 2H), 3.94 (s, 3H), 2.90 (t, 2H), 2.41 (s, 6H), 2.35 (s, 3H).

EXAMPLE 7
6-(2-Dimethylaminoethoxy)-5-methoxy-1-(4'-(1-(methoxyimino)ethyl)-2'-methylbiphenyl-4-carbonyl)-1H-indole Potassium t-butoxide (0.11 g, 1.0 mmole) was added to methanol (10 ml) with stirring under argon and after 20 minutes at room temp. the solution was treated with methoxylamine hydrochloride (0.11 g, 1.3 mmole). The resulting mixture was stirred at room temp. for 20 minutes, then treated with a solution of 1-(4'-acetyl-2'-methylbiphenyl-4-carbonyl)-6-(2-dimethylaminoethoxy)-5-methoxy-1H-indole (E5, 0.30 g, 0.63 mmole) in methanol (10 ml). The mixture was stirred for 18 h at room temp. followed by heating under reflux for 3 h, then concentrated in vacuo. The residue was treated with 10% Na$_2$CO$_3$ solution and extracted with ethyl acetate. The extract was dried (Na$_2$SO$_4$) and concentrated in vacuo to leave a yellow oil, which was chromatographed on silica gel eluting with 0–5% methanol/dichloromethane to afford the title compound (0.20 g, 63%), mp 120°–121° C.

$^1$H NMR (250 MHz, CDCl$_3$) δ (ppm): 8.13 (s, 1H), 7.79 (d, 2H), 7.61 (s, 1H), 7.55 (d, 1H), 7.47 (d, 2H), 7.30-7.22 (m, 2H), 7.05 (s, 1H), 6.53 (d, 1H), 4.25 (t, 2H), 4.03 (s, 3H), 3.92 (s, 3H), 2.89 (t, 2H), 2.41 (s, 6H), 2.33 (s, 3H), 2.26 (s, 3H).

EXAMPLE 8
2,3-Dihydro-6-(2-dimethylaminoethoxy)-5-methoxy-1-(5'-methoxycarbonyl-2'-methylbiphenyl-4-carbonyl)-1H-indole The title compound was prepared from 5'-methoxycarbonyl-2'-methylbiphenyl-4-carboxylic acid (D22) and 2,3-dihydro-6-(2-dimethyl aminoethoxy)-5-methoxy-1H-indole (D14) using a similar procedure to Example 2 as a yellow oil (36%). Conversion to the oxalate salt afforded a white solid. mp 205°–209° C.

$^1$H NMR (free base) (250 MHz, CDCl$_3$) δ (ppm): 8.14 (s, 1H), 8.02-7.95 (m, 2H), 7.82 (d, 2H), 7.50 (d, 2H), 7.39 (d, 1H), 7.24 (d, 1H), 7.06 (s, 1H), 6.55 (s, 1H), 4.25 (t, 2H), 3.93 (s, 3H), 3.92 (s, 3H), 2.90 (t, 2H), 2.42 (s, 6H), 2.37 (s, 3H)

EXAMPLE 9
6-(2-Dimethylaminoethoxy)-5-methoxy-1-(2-methylbiphenyl-4-carbonyl)-1H-indole The title compound was prepared from 2-methylbiphenyl-4-carboxylic acid (D23) and 6-(2-dimethylaminoethoxy)-5-methoxy-1H-indole (D13) using a similar procedure to Example 4 (80%). This was converted to its oxalate salt to afford a white solid. mp 152°–154° C.

$^1$H NMR (free base) (250 MHz, CDCl$_3$) δ (ppm): 8.13 (s, 1H), 7.66 (s, 1H), 7.59 (d, 1H), 7.52-7.32 (m, 6H), 7.27 (d, 1H), 7.06 (s, 1H), 6.53 (d, 1H), 4.26 (t, 2H), 3.93 (s, 3H), 2.91 (t, 2H), 2.42 (s, 6H), 2.35 (s, 3H).

EXAMPLE 10
1-(4'-Acetamidomethyl-2'-methylbiphenyl-4-carbonyl)-2,3-dihydro-6-(3-dimethylaminopropyl)-5-ethoxy-1H-indole The title compound was prepared from methyl 4'-acetamidomethyl-2'-methylbiphenyl-4-carboxylate (D2) and 2,3-dihydro-6-(3-dimethylamino propyl)-5-ethoxy-1H-indole (D29) using a similar procedure to Example 1 (18%). The hydrochloride salt was obtained as a cream coloured solid mp 120°–123° C.

$^1$H NMR (free base) (200 MHz, CDCl$_3$) δ (ppm): 8.05 (br s, 1H), 7.60 (d, 2H), 7.37 (d, 2H), 7.25-7.16 (m, 3H), 6.75 (s, 1H), 6.20 (br s, 1H), 4.45 (d, 2H), 4.20-3.93 (m, 4H), 3.11 (t, 2H), 3.00-2.80 (br, 2H), 2.75-2.50 (br, 8H), 2.28 (s, 3H), 2.15 -1.90 (m, 5H), 1.45 (t, 2H).

I claim:

1. A compound of formula (I) or a pharmaceutically acceptable salt thereof:

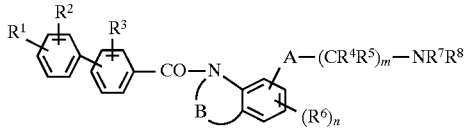

(I)

in which
- $R^1$ is hydrogen, halogen, $C_{1-6}$alkyl, $C_{3-6}$cycloalkyl, $COC_{1-6}$alkyl, $C_{1-6}$alkoxy, hydroxy, hydroxy$C_{1-6}$alkyl, hydroxy$C_{1-6}$alkoxy, $C_{1-6}$alkoxy$C_{1-6}$alkoxy, acyl, nitro, trifluoromethyl, cyano, CHO, $SR^9$, $SOR^9$, $SO_2R^9$, $SO_2NR^{10}R^{11}$, $CO_2R^{10}$, $NR^{10}SO_2R^{11}$, $CONR^{10}R^{11}$, $CO_2NR^{10}R^{11}$, $CONR^{10}(CH_2)_pCO_2R^{11}$, $(CH_2)_pNR^{10}R^{11}$, $(CH_2)_pCONR^{10}R^{11}$, $(CH_2)_pNR^{10}COR^{11}$, $(CH_2)_pCO_2C_{1-6}$alkyl, $CO_2(CH_2)_pOR^{10}$, $CONHNR^{10}R^{11}$, $NR^{10}R^{11}$, $NR^{10}CO_2R^{11}$, $NR^{10}CONR^{10}R^{11}$, $CR^{10}=NOR^{11}$, $CNR^{10}=NOR^{11}$, where $R^{10}$ and $R^{11}$ are independently hydrogen or $C_{1-6}$alkyl and p is 1 to 4;
- $R^2$ and $R^3$ are independently hydrogen, halogen, $C_{1-6}$alkyl, $C_{3-6}$cycloalkyl, $C_{3-6}$cycloalkenyl, $C_{1-6}$alkoxy, acyl, aryl, acyloxy, hydroxy, nitro, trifluoromethyl, cyano, hydroxy$C_{1-6}$alkyl, $C_{1-6}$alkyl$OC_{1-6}$alkyl, $CO_2R^{10}$, $CONR^{10}R^{11}$, $NR^{10}R^{11}$ where $R^{10}$ and $R^{11}$ are independently hydrogen or $C_{1-6}$alkyl;
- $R^4$ and $R^5$ are independently hydrogen or $C_{1-6}$alkyl;
- $R^6$ is hydrogen, halogen, hydroxy, $C_{1-6}$alkyl or $C_{1-6}$alkoxy;
- $R^7$ and $R^8$ are independently hydrogen, $C_{1-6}$alkyl, aralkyl, or together with the nitrogen atom to which they are attached form an unsubstituted or substituted 5–7-membered heterocyclic ring containing one or two heteroatoms selected from oxygen, nitrogen or sulphur;
- A is oxygen, $S(O)_q$ where q is 0, 1 or 2, $CR^4=CR^5$ or $CR^4R^5$ where $R^4$ and $R^5$ are independently hydrogen or $C_{1-6}$alkyl, or A is $NR^{12}$ where $R^{12}$ is hydrogen or $C_{1-6}$alkyl;
- B is $(CR^{13}R^{14})_q$ where q is 2, 3 or 4 and $R^{13}$ and $R^{14}$ are independently hydrogen or $C_{1-6}$alkyl or B is $(CR^{13}R^{14})_r$—D where r is 0, 1, 2 or 3 and D is oxygen, sulphur or $CR^{13}=CR^{14}$;
- m is 1 to 4; and
- n is 1 or 2.

2. A compound according to claim 1 in which $R^1$ is hydrogen, cyano, $COC_{1-6}$alkyl, $(CH_2)_pNR^{10}COR^{11}$ or $CR^{10}=NOR^{11}$.

3. A compound according to claim 1 in which $R^2$ is $C_{1-6}$alkyl.

4. A compound according to claim 1 in which $R^3$ is hydrogen.

5. A compound according to claim 1 in which A is oxygen or $CR^4R^5$ where $R^4$ and $R^5$ are independently hydrogen or $C_{1-6}$ alkyl.

6. A compound according to claim 1 in which m is 2.

7. A compound according to claim 1 which is:
1-(4'-Acetamidomethyl-2'-methylbiphenyl-4-carbonyl)-5-chloro-2,3-dihydro-6-(2-dimethylaminoethoxy)-1H-indole
1-(4'-Cyano-2'-methylbiphenyl-4-carbonyl)-2,3-dihydro-6-(2-dimethylaminoethoxy)-5-methoxy-1H-indole,
1-(4'-Acetyl-3'-methylbiphenyl-4-carbonyl)-2,3-dihydro-6-(2-dimethylaminoethoxy)-5-methoxy-1H-indole,
1-(4'-Acetyl-2'-methylbiphenyl-4-carbonyl)-6-(2-dimethylamino ethoxy)-5-methoxy-1H-indole,
1-(4'-Acetyl-3'-methylbiphenyl-4-carbonyl)-6-(2-dimethylamino ethoxy)-5-methoxy-1H-indole,
1-(4'-Cyano-2'-methylbiphenyl-4-carbonyl)-6-(2-dimethylaminoethoxy)-5-methoxy-1H-indole,
6-(2-Dimethylaminoethoxy)-5-methoxy-1-(4'-(1-(methoxyimino) ethyl)-2'-methylbiphenyl-4-carbonyl)-1H-indole,
2,3-Dihydro-6-(2-dimethylaminoethoxy)-5-methoxy-1-(5'-methoxy carbonyl-2'-methylbiphenyl-4-carbonyl)-1H-indole,
6-(2-Dimethylaminoethoxy)-5-methoxy-1-(2-methylbiphenyl-4-carbonyl)-1H-indole,
1-(4'-Acetamidomethyl-2'-methylbiphenyl-4-carbonyl)-2,3-dihydro-6-(3-dimethylaminopropyl)-5-ethoxy-1H-indole,
or a pharmaceutically acceptable salt thereof.

8. A process for the preparation of a compound of formula (I) which comprises
(a) reaction of a compound of formula (II):

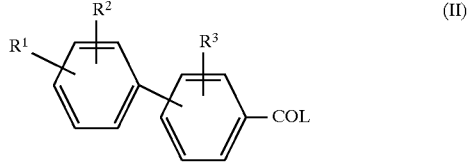

(II)

in which $R^1$, $R^2$ and $R^3$ are as defined in formula (I) and L is a leaving group with a compound of formula (III):

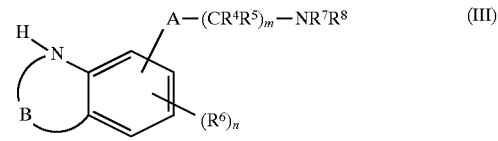

(III)

in which A, m, $R^4$, $R^5$, $R^6$, $R^7$, $R^8$ and n are as defined in formula (I), or
(b) reaction of a compound of formula (III) as defined above with a compound of formula (IV):

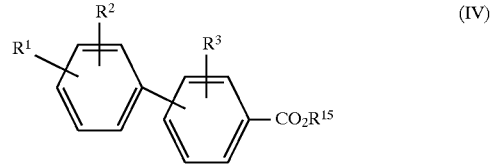

(IV)

in which $R^1$, $R^2$ and $R^3$ are as defined in formula (I) and $R^{15}$ is $C_{1-6}$ alkyl in the presence of a trialkylaluminium reagent; or thereafter:
forming a pharmaceutically acceptable salt.

9. A pharmaceutical composition which comprises a compound according to claim 1 in association with a pharmaceutically acceptable carrier or excipient.

10. A method of antagonizing the $5HT_{1D}$ receptor in a subject which comprises administering an effective amount of a compound of claim 1.

11. A method of treating a disease state selected from the group consisting of: depression, seasonal effective disorder, dysthymia, anxiety, panic disorder, agoraphobia, social phobia, obsessive compulsive disorder, post-traumatic stress disorder, dementia, age-associated memory impairment, anorexia nervosa, bulimia nervosa Parkinson's disease, dementia in Parkinson's disease, neuroleptic-induced Parkinsonism, tardive dyskinesias which method involves treating a patient in need thereof with a therapeutically effective amount of a compound of claim 1.

12. A method of treating a disease state selected from the group consisting of: hyperprolactinaemia, vasospasm, hypertension and sexual dysfunction which method involves treating a patient in need thereof with a therapeutically effective amount of a compound of claim 1.

* * * * *